(12) United States Patent
Owen (10) Patent No.: US 11,173,103 B1
(45) Date of Patent: Nov. 16, 2021

(54) RETINOIDS AND EPIDERMAL STIMULANTS

(71) Applicant: Donald R. Owen, Baton Rouge, LA (US)

(72) Inventor: Donald R. Owen, Baton Rouge, LA (US)

(73) Assignee: Owen Biosciences, Inc., Baton Rouge, LA (US)

( * ) Notice: Subject to any disclaimer, the term of this patent is extended or adjusted under 35 U.S.C. 154(b) by 0 days.

(21) Appl. No.: 16/052,514

(22) Filed: Aug. 1, 2018

Related U.S. Application Data (60) Provisional application No. 62/540,056, filed on Aug. 1, 2017.

(51) Int. Cl.
| | | |
|---|---|---|
| A61K 8/55 | (2006.01) | |
| A61Q 19/08 | (2006.01) | |
| A61K 8/37 | (2006.01) | |

(52) U.S. Cl.
CPC ............... *A61K 8/553* (2013.01); *A61K 8/37* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2008/0287393 A1* | 11/2008 | Sayo | ...................... | A61Q 19/08 514/62 |
| 2013/0095157 A1* | 4/2013 | Jeong | ...................... | A61K 9/51 424/401 |

* cited by examiner

*Primary Examiner* — Dominic Lazaro
(74) *Attorney, Agent, or Firm* — Louis C. Paul (57) ABSTRACT

A novel lysophospholipid concentrate produced by a process comprising the steps of combining (i) a de-oiled lecithin and (ii) from about 0.5 to about 2% of an enzyme with PLA2 activity. The lysophospholipid concentrate is a pourable, homogenous mixture/solution at or about room temperature with has no significant visible precipitate that (a) has an HLB of greater than 12, (b) contains greater than about 20% lysophosphatidylcholine, and (c) contains greater than about 10% lysophosphatidic acid or an LPA-mimetic. Novel low-urea retinoate compounds produced by the reaction of (a) retinoic acid and (b) one or both of glycerine and/or a monoacylglyceride in the presence of a carbodiimide coupling agent, and preferably in the presence of p-toluene sulfonic acid. The low-urea retinoate is a pourable, homogenous mixture/solution at or about room temperature with no significant visible precipitate.

13 Claims, 8 Drawing Sheets

RETINOIDS AND EPIDERMAL STIMULANTS

FIELD OF INVENTION

Topical compositions that contain at least one retinoid and a lysophospholipid concentrate and uses of such compositions to reduce one or more signs of chronological or environmental skin aging.

BACKGROUND OF THE INVENTION

Keratinocytes proliferate in the basal layer and move upward into the supra basal layers. In these supra basal layers—the stratum *spinosum* and stratum *granulosum* (i.e., granular layer)—keratinocytes differentiate. Keratinocyte differentiation ends with programmed cell death and conversion into corneocytes (anuclear cellular "remnants" devoid of intracellular organelles). Terminally differentiated (granular) keratinocytes compose the last "living" layer of skin, and produce a majority of the lipids and proteins composing the stratum corneum; they are regularly replaced through desquamation and upward migration of cells from the lower epidermal layers.

Retinoids are some of the most widely common "proliferative" ingredients in aesthetic dermatology and cosmetic skincare. Among the benefits associated with these ingredients are decreases in the appearance of surface roughness, discoloration, solar keratoses, fine lines and wrinkles, and overall pigmentation as well as increases in density of collagen and improvement in quality of elastin fibers.

It is well known in the dermatologic art that topical application of formulations that contain a retinoid can, and often do, result in negative sequelae, including flaking, inflammation, erythema, decreased skin barrier function, and increased sensitivity to other cosmetic and skincare ingredients and environmental stressors. Importantly, these negative sequelae lead to reduced levels of keratinocyte proliferation and accelerated/incomplete terminal differentiation of keratinocytes into corneocytes. The result—reduced epidermal thickness and decreased skin barrier function—makes skin even more susceptible to environmental insult, and further damage; perpetuating a cycle that results in visible skin aging.

Skin Physiology: The "epidermis" is stratified, cornified epithelium comprised of four layers of cells—named for their relative position or a structural property. From bottom to top, the layers of the epidermis are: (i) the stratum basale, also known in the art as stratum germinativum, and referred to in this application as the basal layer ("BL"); (ii) the stratum *spinosum*, referred to herein as the spinous layer ("SL"); (iii) the stratum *granulosum*, referred to in the present application as the granular layer ("GL"); and (iv) the stratum corneum ("SC").

Attached to the basement membrane of the dermal-epidermal junction ("DEJ"), the BL is comprised of mitotically-active, columnar-shaped keratinocytes. As discussed below, basal cells are characterized by expression of KRT5 and KRT14, genes that code, respectively for keratin 5 (K5) and keratin 14 (K14).

Transit amplifying ("TA") cells, produced by division of BL stem cells, are the most common cells in the BL and account of the majority of cell divisions needed for stable (i.e., homeostatic) self-renewal of the BL. See, e.g., J A Lechler and E Fuchs, "Asymmetric cell divisions promote stratification and differentiation of mammalian skin," Nature Vol. 437, No. 7056, pp. 275-280 (2005). TA cells give rise to post-mitotic epidermal basal cells, which undergo "keratinization" (defined immediately below).

"Keratinization" (also referred to in the present application as "keratinocyte differentiation") is a gene-regulated series of morphologic changes and metabolic events ending in dead keratinocytes (corneocytes) that contain keratin filaments, matrix proteins, and a protein-reinforced plasma membrane with surface-associated lipids. In humans, at least 14 days are typically required for a BL cell to enter the SC; transit through the SC and subsequent desquamation typically requires another 14 days. As described below, these time periods can be, and are altered, by administration of retinoids, resulting in hyperproliferative or growth-arrested states.

SL cells—so described for the spine-like appearance of the cell margins after H&E (hematoxylin and eosin) staining—are polyhedral in shape with a rounded nucleus. As these cells differentiate and move upward through the epidermis, they become progressively flatter, developing into "lamellar granules" of the SG. Histologically SL cells begin to flatten and "pack".

SG cells are flattened and granulated. Keratohyalin granules are prominent within the SG.

Collectively, SL and GL cells are sometimes referred to herein as "supra-basal".

As discussed below, supra basal cells are characterized by expression of KRT1 and KRT10, genes that code, respectively for keratin 1 (K1) and keratin 10 (K10).

Terminally (i.e., completely) differentiated GL keratinocytes are stacked in layers of anucleate, flattened cornified cells, forming the SC. These anuclear cellular "remnants" are devoid of intracellular organelle and are more commonly referred to in the art as "corneocytes."

The SC is formed by corneocytes surrounded by a lipid extracellular matrix (ECM). Together, these two components provide a protective barrier to water loss, and damage from environmental stressors including UV radiation. In addition to providing mechanical reinforcement and hydration, the ECM provides protection by antimicrobial peptide activity and cytokine-mediated initiation of inflammation. See J A Segre, "Epidermal barrier formation and recovery in skin disorders," *J Clin Invest*, Vol. 116, No. 5, pp. 1150-1158 (2006); see also, P M Elias, "Stratum corneum defensive functions: An integrated view," *J Invest Dermatol, Vol.* 125, No. 2, pp. 183-200 (2005).

Important to a well-differentiated epidermis µone that provides protection from mechanical, physical, chemical or microbial insults—are cell-cell and cell-basement membrane adhesion in the epidermis.

Desmosomes are responsible for adhesion within the layers of the epidermis, anchoring cytoskeletal filaments to cell-cell junctions. Desmosomes are comprised of the desmosomal proteins: cadherins (desmogleins and desmocollins), plakins (desmoplakin, envoplakin, and periplakin), and armadillo family proteins (plakoglobin and plakophilins).

Adhesion at the dermal-epidermal junction is dependent on the number and quality of hemidesmosome-basement membrane adhesion complexes and related structures. Hemidesmosomes (comprised of plakin homologs, integrins, and collagenous transmembrane proteins) anchor cytoskeletal filaments of BL cells to the basement membrane. More particularly, laminin 5—a key constituent of the basement membrane—binds directly to type VII collagen, forming anchoring fibrils that bind to transmembrane integrin $\alpha 6\beta 4$, found in the hemidesmosome. Niessen et al., *Exp Cell Res.*, Vol. 211, No. 2, pp. 360-7 (1994). Laminin 5 also forms complexes with laminin 6 and 7. These complexes bind with type IV collagen, creating the basement membrane cytoskeleton.

Homeostasis and Dermal Hyperproliferation: The BL synthesizes two keratin "partners," K5 and K14. These structurally-similar proteins form "keratin intermediate filaments", which assemble into strong networks that help attach keratinocytes together and anchor the epidermis to underlying dermis.

Under homeostatic conditions, SL cells primarily synthesize two keratins, K1 and K10—both known in the art as "differentiation-specific" or "keratinization-specific" keratins. K1 and its K10 partner form keratin intermediate filaments that provide strength, resiliency and protection to the skin (e.g., from externally-caused damage, including environmental stressors like UV radiation). SL cells also retain K5 and K14 (produced in the BL).

mRNA for keratins K6 and K16 is present throughout the epidermis; but messages for these proteins are not translated until stimulation of proliferation.

In response to hyperproliferative conditions (including wound healing, psoriasis, and actinic keratoses) the following occur: (a) synthesis of K1 and K10 proteins, as well as K1 mRNA and K10 mRNA, is downregulated; (b) synthesis and translation of messages for keratins K6 and K16 increase; and (c) SL cells can synthesize new mRNA for K5 and K14.

Changes in keratin expression from hyperproliferation can result in a disruption of "normal differentiation" of the GL cells into cornified SC cells.

Application of all trans retinoic acid at a concentration of 0.1% or all trans retinol at a concentration of 1.0% to the skin of mice stimulates basal cell turn over but inhibits or suppresses the formation of normally-functioning supra basal granular keratinocytes. For example, de minimis or no flattening of the oval supra basal cells is observed; and de minimis or no granular formation is observed. The resulting SC formed is weak, poorly held together and produces little barrier protection. This is characterized by flaking, peeling, and possible increased trans-epidermal water loss.

Because prior art retinol and retinoic acid compositions can and do have significant negative sequelae in humans—causing sensitivity to the retinol or retinoic acid composition itself and/or to other dermatologic or skincare formulations, and, in many cases, causing the user (patient or consumer) to entirely stop treatment. The methods of the present invention enable the effective use of lower doses of retinol (i.e., clinically demonstrable effects on reducing the signs of chronological or environmental skin aging) with little or no peeling or flaking, and without negatively impacting (i.e., suppressing by 20% or more) the production of lipids, ceramides, adhesion proteins, or defensins by the granular keratinocytes.

Conjugated retinol derivatives and conjugated retinoic derivatives require more time to achieve a comparable epidermal thickening as their non-conjugated retinol "parent" compound. In order to produce similar clinical results (in terms of epidermal thickening) as a non-conjugated retinol over a similar timeframe, the prior art dose of conjugated retinol derivative (or a conjugated retinoic derivative) is typically doubled. At that "doubled-dose", however, conjugated retinol derivatives (as well as conjugated retinoic derivatives) are, nonetheless, slower in eliciting the desired improvement (reduction in signs of chronological or environmental skin aging), are significantly more expensive (than non-conjugated parent molecules) and can cause visible skin redness.

Even tripling conjugated retinoid concentrations does not lead to significant improvements in basal cell turnover rates. In the absence of a concomitant administration of a lysophospholipid concentrate visible reduction in the signs of chronological or environmental skin aging in slow; often 4-6 weeks of use conjugated retinoids are required before significant skin improvements can be noted. Given the demand and expectation for near-immediate results, many consumers grow impatient and discontinue conjugated retinoid skincare regimens.

Glyceryl diretinoate (GDR) has been included in prior art skincare formulations, including R45 The Reversal 3-Phase Skin Transforming Treatment from Beauty Bioscience, Inc. GDR in this and other prior art products is different than the low-urea retinoate of the present invention. Prior art GDR contained 30% (or more) retinoyl urea, a crystalline material that has no bioactivity as a dermal proliferative. The present application relates to low-urea retinoates, including novel forms of GDR having very low levels of retinoyl urea, preferably less than 0.1%. By minimizing crystallization, low-urea GDR of the present invention is considerably more bioactive and can be used at significantly lower concentrations with better results than prior art GDR.

Methods of skin treatment in accordance with the present invention produce epidermal thickening at a rate similar to non-conjugated retinoic acid, but significantly less suppression of production of defensins, lipids, ceramides, and adhesion proteins typically associated with retinoic acid use.

There has been and remains a need for methods of skincare that improve the quality of chronological or environmentally aged skin—by decreasing roughness (improving smoothness); reducing discoloration, solar keratoses, and overall pigmentation; increasing density of collagen; improving quality of elastin fibers—without negatively impacting (i.e., decreasing) skin barrier function (reducing epidermal thickness and increasing trans-epidermal water loss), without causing visible irritation and without reducing levels of protective skin antimicrobial proteins (defensins). Those needs are met by the methods of the present invention.

BRIEF DESCRIPTION OF THE FIGURES

Photomicrographs of murine tissue samples treated according to methods of the present invention are presented the figures. Differing amounts of inter-laminar keratinocyte differentiation were observed. In some cases, there is intralaminar disruption, in which stratum corneum (SC) and granular layer (GL) are separated, indicating little granular keratinocyte formation and/or suppression of one or both of granular keratinocyte extracellular desmosomal proteins and/or reduced production of laminar granules (proteases, lipids). This was not considered an artifact of the microtome blade.

SUMMARY OF THE INVENTION

Figure 1:
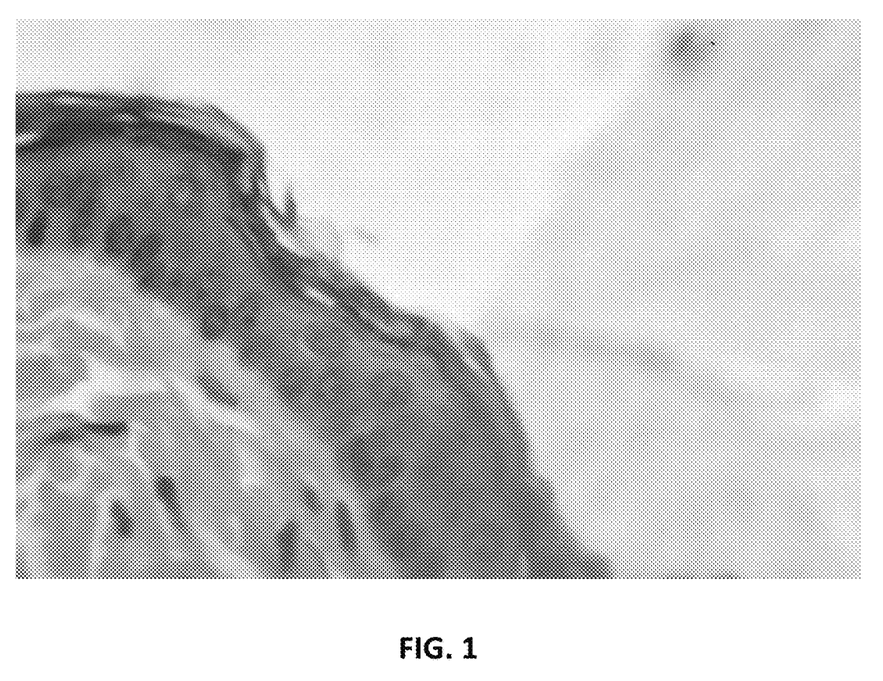
FIG. 1 is a photomicrograph of a punch biopsy of mature murine skin after application of retinol (ROH) at 0.25%, retinyl safflowerate (RS) at 0.5% and phospholipid (lecithin containing about 85% phosphatidylcholine, PL85) at 0.2%.
Figure 2:
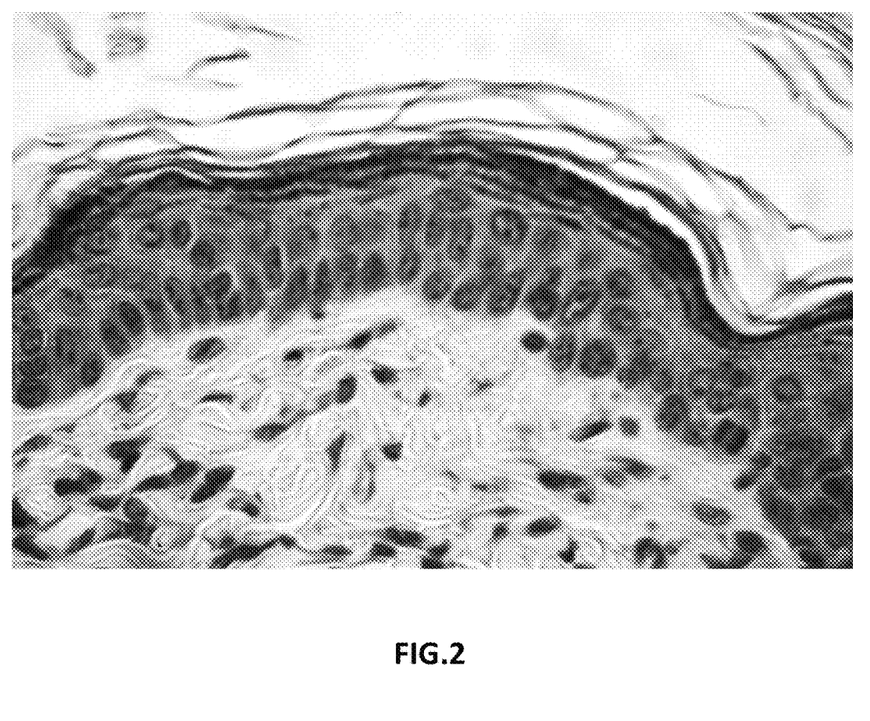
FIG. 2 is a photomicrograph of a punch biopsy of mature murine skin after application of the same formulation as FIG. 1—ROH (0.25%), RS (0.5%), PL85 (0.2%)—with the addition of 0.1% of an LPA-mimetic, oleoyl glyceryl phosphate (OGP).
Figure 3:
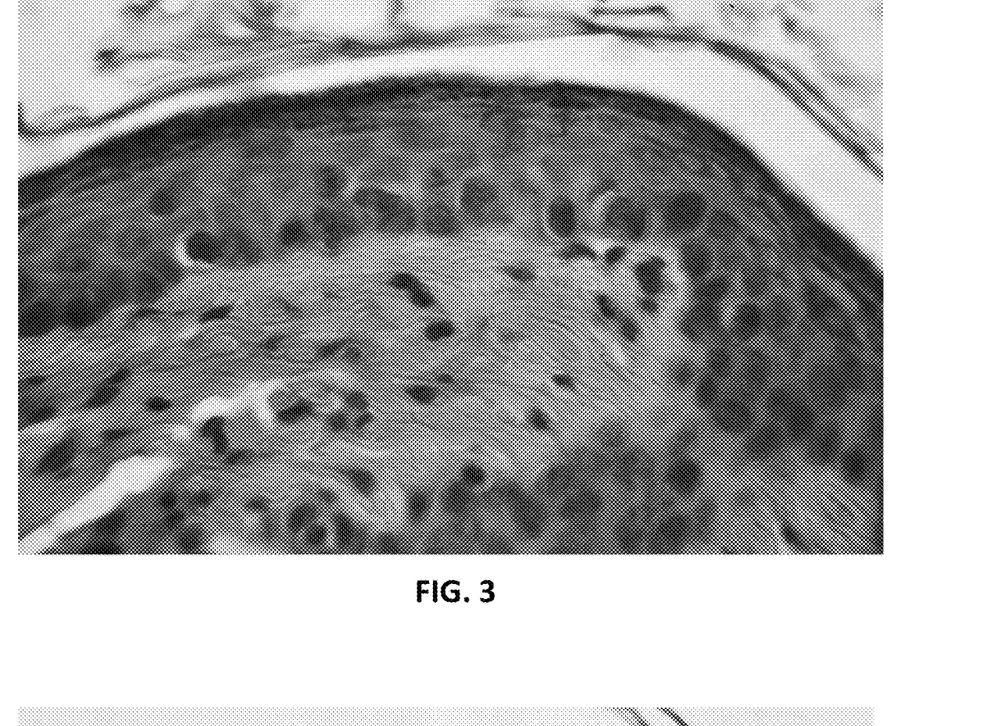
FIG. 3 is a photomicrograph of a punch biopsy of mature murine skin after application of the same dermal proliferative and ester as FIG. 1—ROH (0.25%) and RS (0.5%)—with the addition of 0.2% of a lysophospholipid concentrate of the present invention formed by reacting 98% lecithin (having a monoester content of greater than 90%) with 2% phospholipase A2 (PLA2).
Figure 4:
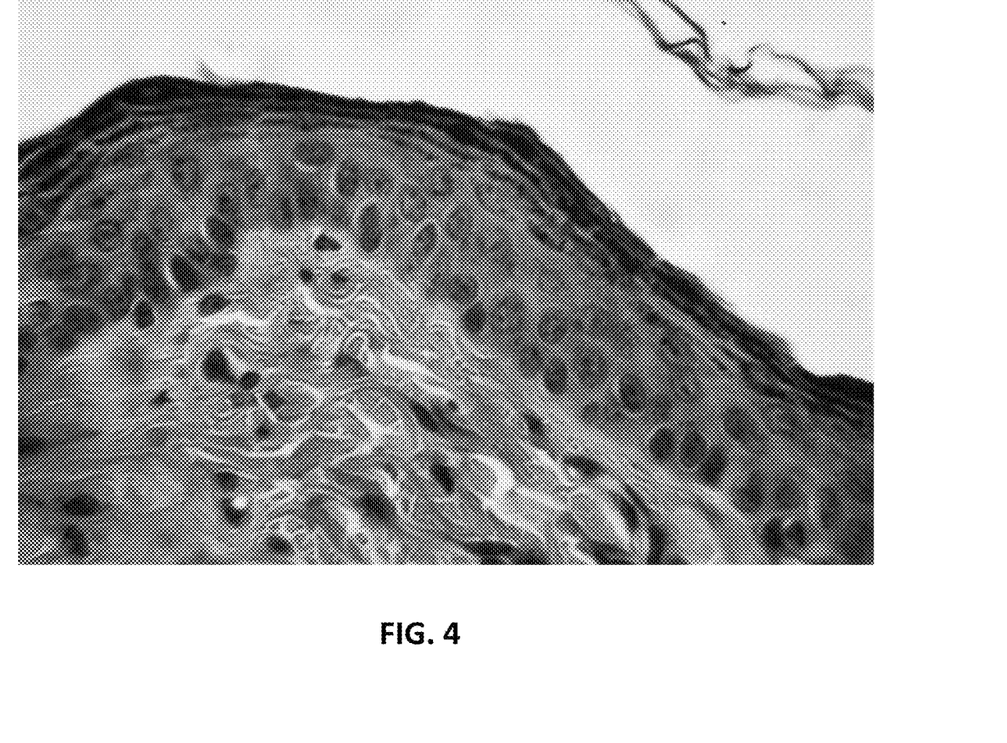
FIG. 4 is a photomicrograph of a punch biopsy of mature murine skin after application of the same formulation as FIG. 3—ROH (0.25%), RS (0.5%) and 0.2% of the lysophospholipid concentrate of the present invention—with the addition of 0.1% OGP.
Figure 5:
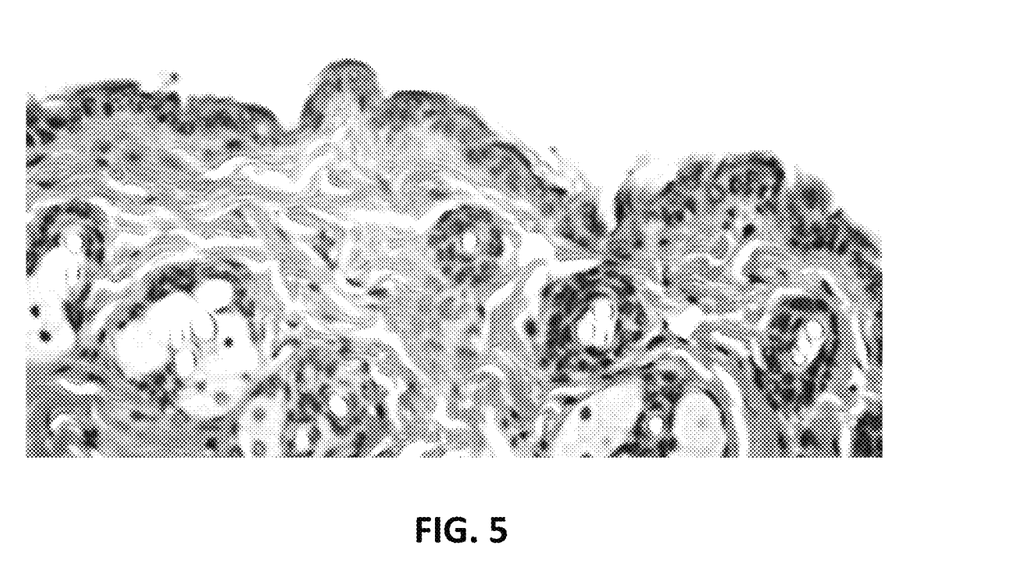
FIG. 5 shows mature murine skin with no treatment (no bioemulsion as defined immediately below).
Figure 6:
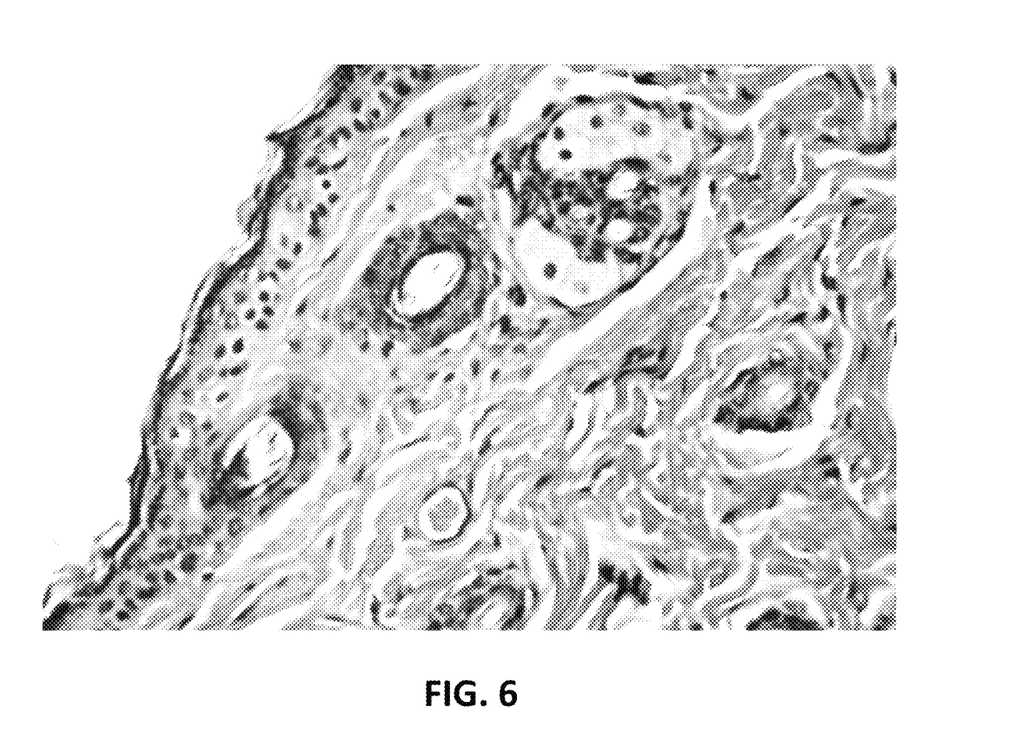
FIG. 6 shows mature murine skin after topical application of the bioemulsion, but without a dermal proliferative. By the term "bioemulsion" is meant a surfactant/emulsifier that can be enzymatically reduced in vivo into sugars, glycerides, fatty acids or amino acids. The same bioemulsion was used in the FIGS. 8-22.
Figure 7:
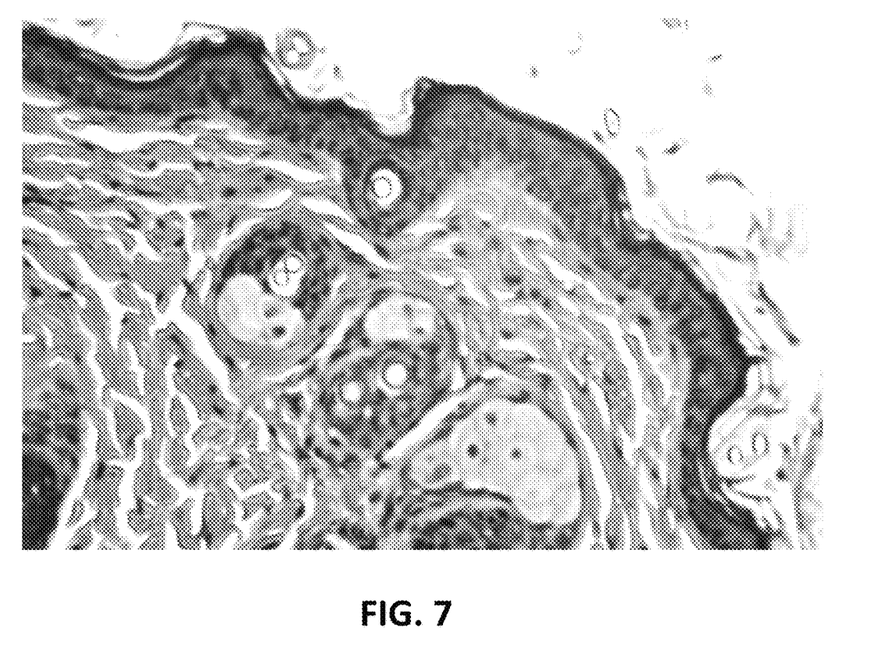
FIG. 7 shows the effect of the same bioemulsion in FIG. 6 with the addition of 1% retinyl linoleate. Increased proliferation and SC density are observed, but without significant differentiation.
Figure 8:
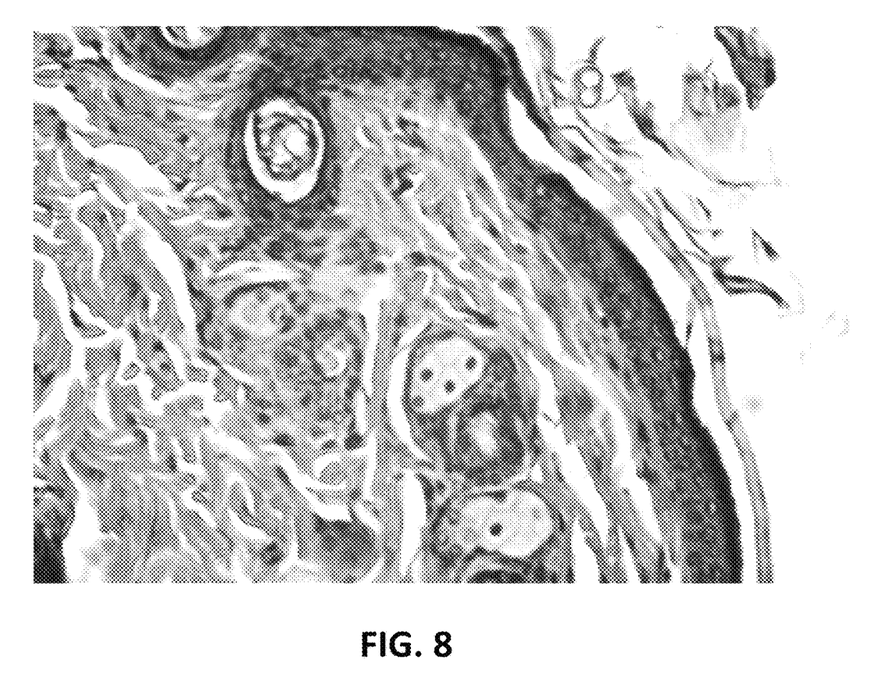
FIG. 8 shows the effect of the same emulsion in FIG. 6 with the addition of 1% retinyl linoleate and 0.10% OGP. Increased SC density and thickness are observed.
Figure 9:
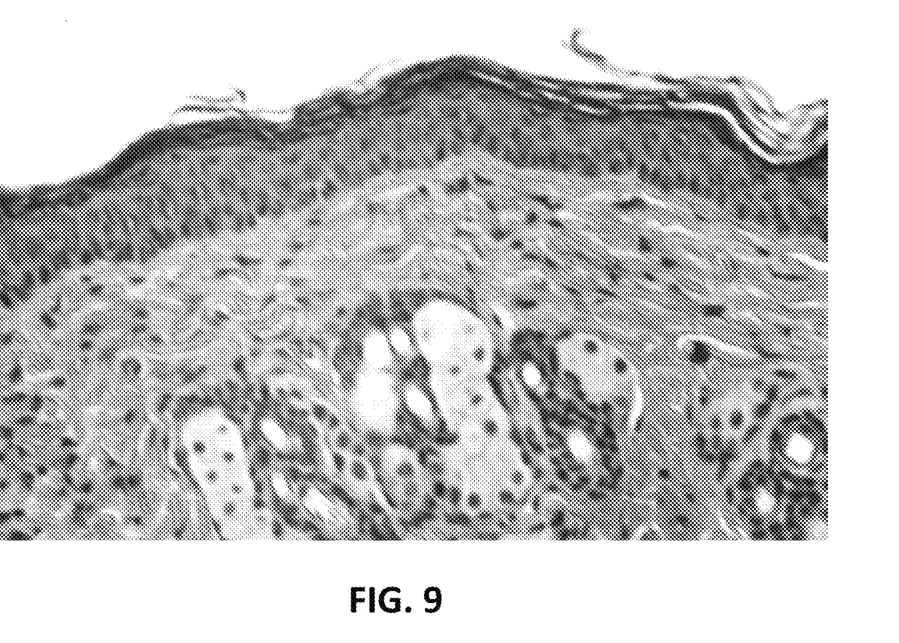
FIG. 9 shows the effect of the same bioemulsion in FIG. 6 with the addition of 1% retinyl linoleate and 0.25% OGP. Keratinocyte differentiation is well defined. Significant increase in cornification and SC thickness are observed.
Figure 10:
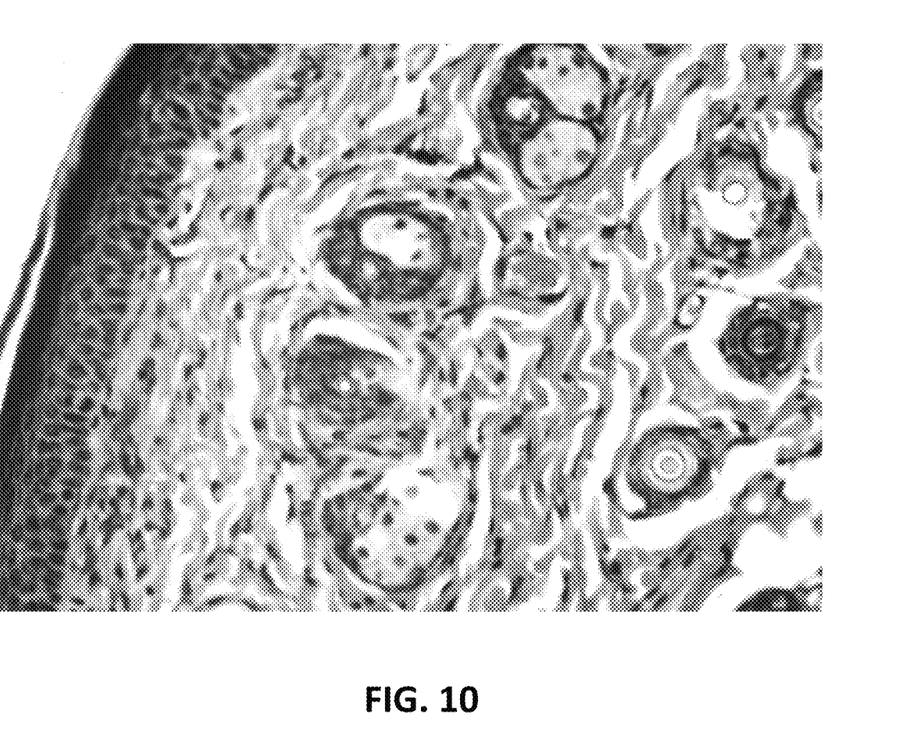
FIG. 10 shows the effect of the same bioemulsion in FIG. 6 with the addition of 1% retinyl linoleate and 0.5% OGP. A thicker, very dense SC with significant differentiation is observed. Increased fibroblast activity is also noted.
Figure 11:
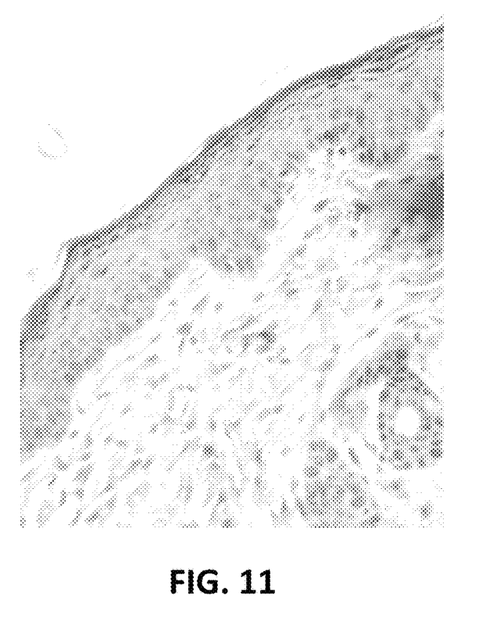
FIG. 11 shows the effect of 1% glyceryl diretinoate in a bioemulsion applied once daily over two consecutive days. Both good proliferation and differentiation were observed.
Figure 12:
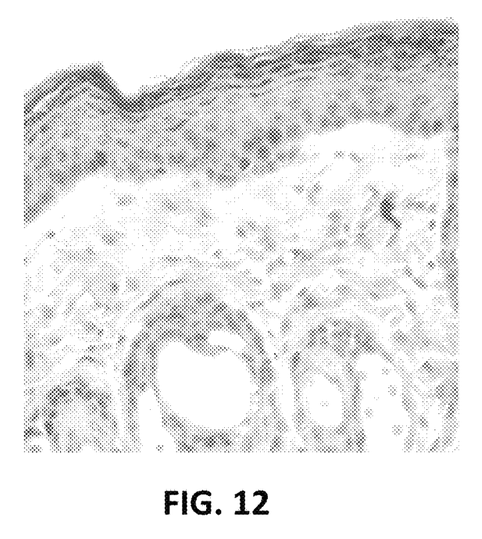
FIG. 12 shows the effect of 1% glyceryl oleoyl retinoate in a bioemulsion applied once daily over three consecutive days.
Figure 13:
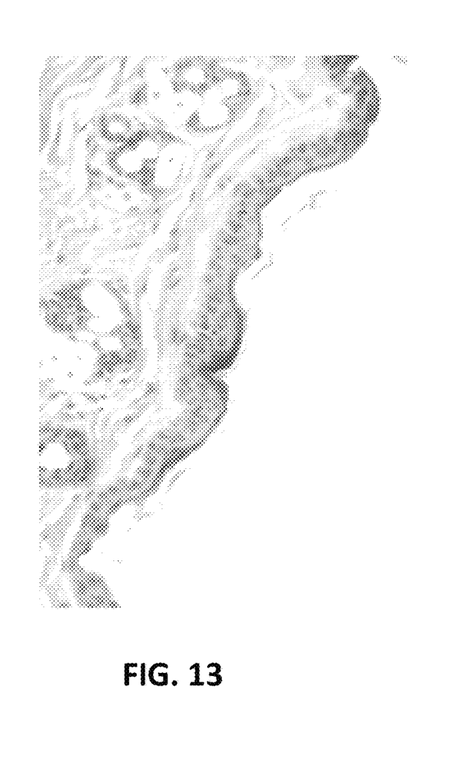
FIG. 13 shows the effect of diretinyl succinate in a bioemulsion applied once daily, for 4 consecutive days. De minimis proliferation was observed, with de minimis keratinocyte differentiation.
Figure 14:
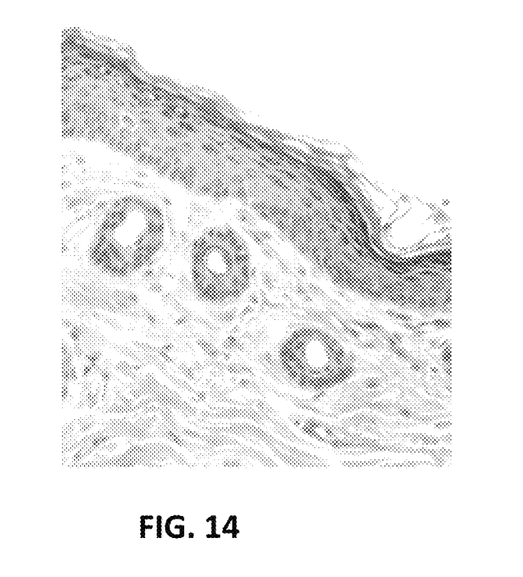
FIG. 14 shows the effect of 1% acetyl-n-phenylalanine retinoate in a bioemulsion applied once daily over three consecutive days. Both good proliferation and differentiation were observed.
Figure 15:
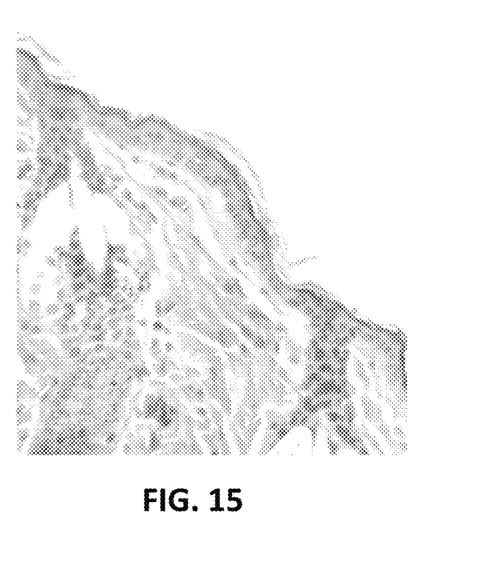
FIG. 15 shows the effect of 1% retinyl phosphate in a bioemulsion applied once daily over 4 consecutive days. De minimis proliferation was observed, with de minimis keratinocyte differentiation.
Figure 16:
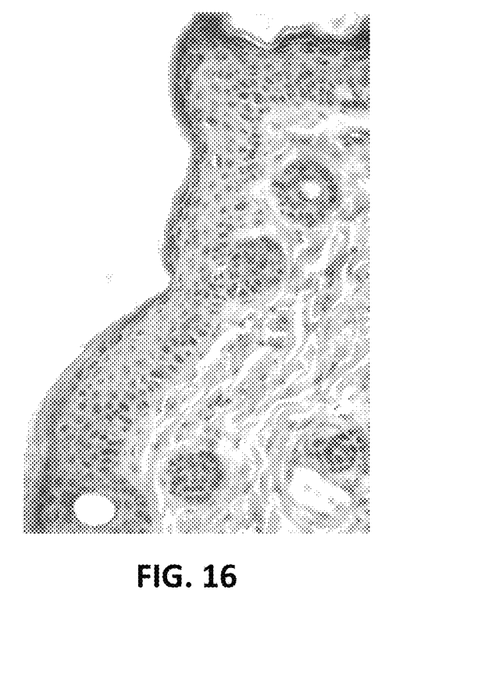
FIG. 16 shows the effect of 1% glyceryl mono retinoate in a bioemulsion applied once daily over 2 consecutive days. Both excellent proliferation and differentiation were observed.
Figure 17:
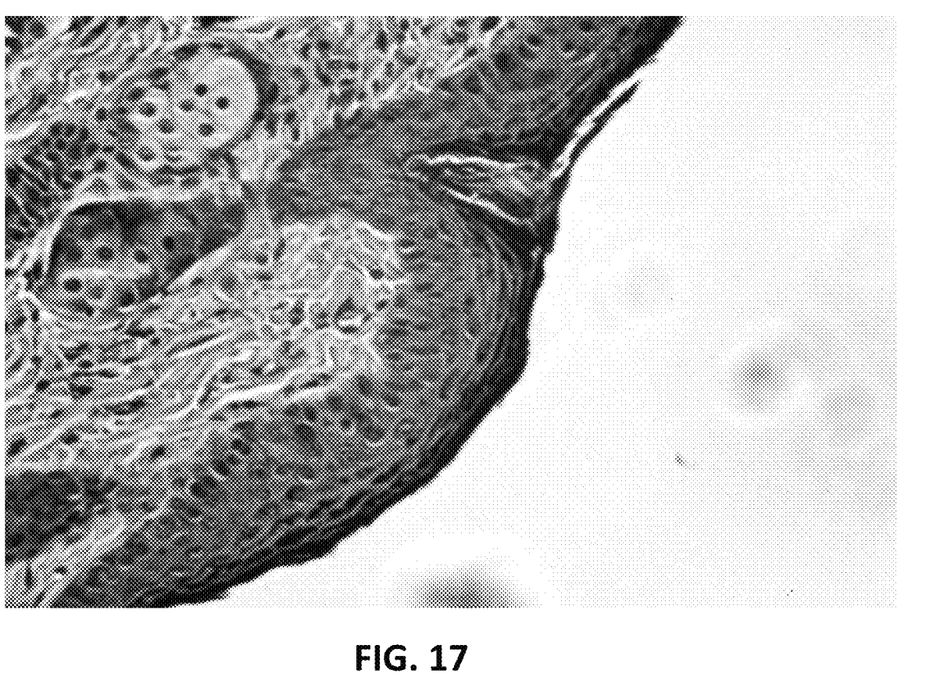
FIG. 17 and FIG. 18 illustrate, respectively, GDR at 0.5% and GDR at 2.0% administered once daily, over three consecutive days, in anhydrous dermatocosmetic composition.
Figure 18:
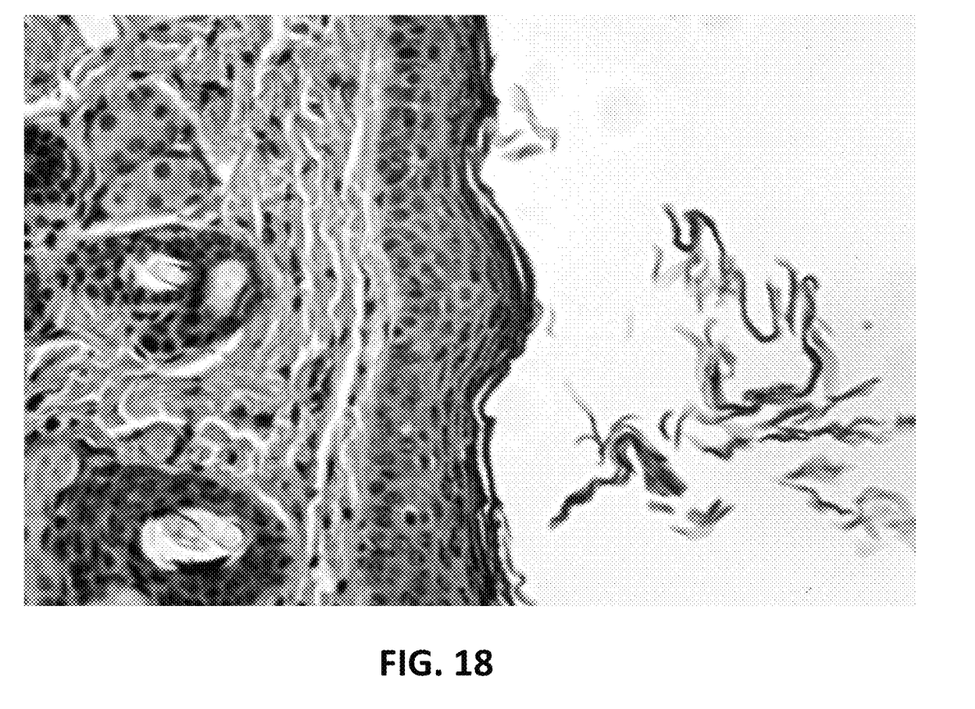

A first aspect of the present invention is directed to a novel lysophospholipid concentrate produced by a process comprising the steps of combining (i) a de-oiled lecithin and (ii) from about 0.5 to about 2% of an enzyme with PLA2 activity. The lysophospholipid concentrate is a pourable, homogenous mixture/solution at or about room temperature with has no significant visible precipitate that (a) has an HLB of greater than 12, (b) contains greater than about 20% lysophosphatidylcholine, and (c) contains greater than about 10% lysophosphatidic acid or an LPA-mimetic. Preferably, the lysophospholipid concentrate contains an LPA-mimetic (a mono-oleoyl glyceryl phosphate or a cyclic derivative thereof) and/or LPA at a concentration of from 10 to 50%.

A second aspect of the present invention is directed to novel low-urea retinoate compounds produced by the reaction of (a) retinoic acid and (b) one or both of glycerine and/or a monoacylglyceride in the presence of a carbodiimide coupling agent, and preferably in the presence of p-toluene sulfonic acid. The low-urea retinoate is a pourable, homogenous mixture/solution at or about room temperature with no significant visible precipitate.

The invention is further directed to use of one or both of the above-described novel ingredient technologies to reduce the chronological or environmental skin aging without flaking or peeling of the epidermis, and visible skin redness.

DETAILED DESCRIPTION OF THE INVENTION

Prior art methods for reducing one or more signs of "chronological or environmental skin aging" (defined below) focused on thickening the epidermis via administration of non-conjugated retinoids, conjugated retinol derivatives, conjugated retinoic acid derivatives (collectively retinoids, each defined below). However, achieving the desired increase in epidermal thickness with retinoids—preferably at least about 20%, more preferably at least about 30%, still more preferably at least about 40%, and even more preferably at least about 50%—required administration at concentrations and/or a dosing regimen that cause one or more of "deleterious skin effects" (defined below)—typically, increased flaking or peeling of the epidermis, and visible skin redness.

The new states of matter and dermatocosmetic compositions containing those new states of matter (in combination with retinoids of the prior art) achieve optimized epidermal thickening (and thereby reduce one or more signs of chronological or environmental skin aging) at levels comparable to prior art retinoids, but without (i) negatively impacting skin barrier function; (ii) causing an increase in flaking or peeling; or (iii) visibly increasing skin redness.

Increased epidermal thickening, lack of a negative impact on skin barrier function, and lack of visible increase in skin redness is measured instrumentally and/or by histology.

Changes in epidermal thickness can be expressed in terms of ultrasound readings or histological examination (stained tissue samples from punch biopsies under microscope).

More particularly, histological observations, including degree of "keratinocyte differentiation" are described by reference to photomicrographs of retired breeder mice obtained from Charles River Laboratories, Inc. (Wilmington, Mass.). An area of approximately one square inch was shaved. Test compositions (e.g., control=carrier vehicle with ingredient known to be irritating; test=same carrier and known irritant from control+phospholipid) were administered in accordance with methods of the inventions. Punch biopsies of full thickness skin and subcutaneous fat were taken as follows: skin was swabbed with an antiseptic and injected with a local anaesthetic; an incision was made, and a tissue specimen was removed and preserved in 10% neutral buffered formalin at a volume of approximately ten times that of the tissue). Excision sites were sutured. The preserved tissues samples were sent to Louisiana State University, School of Veterinary Medicine for processing and analysis. More particularly, tissue was processed in graded alcohol [70% (v/v) ethanol, 90% (v/v) ethanol, absolute ethanol] followed by graded xylene [70% (v/v) ethanol, 90% (v/v) ethanol, absolute xylene]. Next the processed tissue was placed in blocks/molds filled with paraffin wax liquid, in an orientation with the epidermis on top, with ice on top to hold the tissue in place. Wax blocks were cooled in ice and sectioned at a thickness of 5-15 μm using a microtome with disposable blade (Leica Microtome Model RM2255). Microtomed sections were placed on adhesive slides, incubated at 37° C. for 24 hours (i.e., on slide racks), and then stored in slide containers at room temperature until H&E staining is performed to visualize histological microstructures. All histological samples were micro photographed at 400× under normal light with standard digital equipment. These photos were transferred to PHOTOSHOP® computer imaging software from Adobe Systems Pvt. Ltd., in which measurements of epidermal thickness, SC thickness, granulation, layering were determined.

Changes in skin barrier function can be expressed in terms of changes in trans-epidermal water loss and/or histology (degree of differentiation cells or separation of cell layers, for example, separation of the stratum corneum from the underlying stratum lucidum and/or interlamellar separation among the stratum *spinosum* and stratum *granulosum*). Changes in barrier function can also be measured by tape stripping.

Changes in skin redness can be measured by the naked eye of a trained observer, by a chromameter, or in terms of irritation based on changes in level of expression of cytokines and other proteins.

Definitions

"Signs of chronological or environmental skin aging" means one or more of (i) increases in number, length and/or depth of lines, wrinkles, furrows; (ii) decreased skin elasticity as measured with a ballistometer or ultrasound probe, and as physically manifested, for example, in sagging; (iii) decreased skin barrier function, as measured as increased trans-epidermal water loss; (iv) decrease in the quantity of collagen fibers and the presence of inflammatory infiltrate; (v) flattening of rete pegs at the dermoepidermal junction. See, e.g., Z. Draelos, "Topical Treatments for Benign Photodamage" in D. Goldberg (ed.), Photodamaged Skin, pp. 146-147 (2004).

"Deleterious skin effect" means one or more of (a) peeling and/or flaking of the epidermis, (b) erythema, upregulation of one or more genes that code for a pro-inflammatory protein, the pro-inflammatory protein gene selected from the group of CASP1, TNF, IL1A, and IL1B, (c) incomplete differentiation of keratinocytes in the stratum *granulosum* or stratum *spinosum*, (d) reduced expression of a defensin protein, especially DEFB1, (e) reduced expression of one or more growth factor genes associated with cell turnover and fibroblast crosstalk selected from the group of HBEGF, TGFB1, TGFA, FGF2 and CSF2, and/or (f) reduced expression of one or more genes that code for a corneo-desmosomal protein, including but not limited to DSG2.

By the phrase "poor inter-laminar adhesion" is meant the loss or under expression of one or more genes that code for desmosomal proteins or proteins that form hemidesmosome-basement membrane adhesion complexes.

"De-oiled lecithin" means crude lecithin from a plant source, preferably soybeans or oilseeds selected from the group of rapeseed, sunflower seed, or maize, that undergoes one or more of filtration, deodorization, fractionation or enzymatic modification to remove triglycerides.

An "enzyme with PLA2 activity" means a phospholipase A2 enzyme, namely phosphatide-2-acyl-hydrolase.

"Lecithin" is a complex mixture of phosphatides, consisting chiefly of phosphatidylcholine, phosphatidylethanolamine, phosphatidylserine, and phosphatidylinositol, with varying amounts of triglycerides, fatty acids, and carbohydrates isolated from animal or vegetable sources.

"Lysolecithin" is the product obtained from acid, enzyme or other method of hydrolysis of lecithin. In preferred methods of the present invention, lecithin is partially and selectively hydrolyzed, producing monoacyl phosphatidyl choline (as well as other phosphatides).

"Phosphatidylcholine" contains two acyl group and conforms to the formula:

"Lysophosphatidylcholine" ("LysoPC") is the hydrolysate of phosphatidylcholine obtained by acid, enzyme or other method of hydrolysis, preferably by selective enzyme hydrolysis with PLA2. It is a monoglycerophospholipid in which a phosphorylcholine moiety occupies a glycerol substitution site. LyosPCs can have different combinations of fatty acids of varying lengths and saturation. The fatty acids are attached at the C-1 (sn-1) position. Fatty acids containing 16, 18 and 20 carbons are the most common.

"Phosphatidylethanolamine" is the phospholipid that conforms to the formula:

where RCO— represents various naturally occurring fatty acids.

"Lysophosphatidylethanolamine" also known in the art as monoacylglycerophospho-ethanolamine is the hydrolysate of phosphatidylethanolamine obtained by acid, enzyme or other method of hydrolysis, preferably by selective enzyme hydrolysis with PLA2.

"Phosphatidylinositol" is the phospholipid that conforms to the formula:

where RCO— represents naturally occurring fatty acids.

"Lysophosphatidylinositol" is the hydrolysate of phosphatidylinositol obtained by acid, enzyme or other method of hydrolysis, preferably by selective enzyme hydrolysis with PLA2.

"Phosphatidylserine" is the phospholipid that conforms to the formula:

where RCO— represents naturally occurring fatty acids.

"Lysophosphatidylserine" is the hydrolysate of phosphatidylserine obtained by acid, enzyme or other method of hydrolysis, preferably by selective enzyme hydrolysis with PLA2.

"Phosphatidic Acid" (diacylglycerol phosphate) is a phospholipid in which one of the primary hydroxyl groups of glycerin is esterified with phosphoric acid; and the two remaining hydroxyl groups (of glycerin) are esterified with long chain, saturated or unsaturated fatty acids.

"Lysophosphatidic acid" (abbreviated "LPA" also known as mono-acylglycerol phosphate) is a lysoglycerophospholipid that conforms to the formula:

where RCO— represents a long chain saturated or unsaturated fatty acid, and a phosphate moiety occupies a glycerol substitution site. Different combinations of fatty acids of varying lengths and saturation attached at the C-1 (sn-1) or C-2 (sn-2) position; fatty acids containing 16 and 18 carbons are the most common.

"Oleoyl glyceryl phosphate" (abbreviated "OGP"; and also referred to as mono-oleoyl glyceryl phosphate) can be made by either (i) phosphorylation of a "predominantly mono-acyl glyceride" (i.e., a glyceride one having a monoester content of greater than about 90%) or (ii) reaction of glyceryl phosphate and oleoyl acid chloride.

In describing the present invention, OGP is also referred to as an "LPA-mimetic" by which is meant OPG contains naturally-occurring LPA or an isomer of LPA.

"Retinoid" means natural and/or synthetic analogs of Vitamin A or compounds which possess the biological activity of Vitamin A in the skin as well as the geometric isomers and stereoisomers of these compounds, such as all-trans retinoic acid and 13-cis-retinoic acid.

In addition to the retinoids described in the following paragraphs, the term retinoid is also to be understood to include adapalene {6-[3-(1-adamantyl)-4-methoxyphenyl]-2-naphthoic acid}; tazarotene (ethyl 6-[2-(4,4-dimethylthiochroman-6-yl)-ethynyl]nicotinate; and the retinoid compounds described in the following U.S. patents, the disclosures of which are incorporated herein, in pertinent part, by reference in their entirety: U.S. Pat. Nos. 4,677,120; 4,885,311; 5,049,584; and 5,124,356.

"Non-conjugated retinoid" means (a) all trans retinol, (b) all trans retinaldehyde, and (c) all trans retinoic acid, each defined below.

Retinoic acid ($C_{19}H_{26}O_2$) is the organic compound that conforms to the formula:

Retinol ($C_{20}H_{30}O$) is the organic compound that conforms to the formula:

Retinal ($C_{20}H_{28}O$) is the organic compound that conforms to the formula:

"Conjugated retinol derivative" means $C_2$-$C_{22}$ alkyl esters of retinol (preferably retinyl linoleate, retinyl palmitoleate, retinyl oleate) and acetylated retino-amino acids.

Retinyl linoleate is the ester of retinol (q.v.) and linoleic acid (q.v.).

Retinyl palmitoleate is the ester of retinol (q.v.) and linoleic acid (q.v.).

Retinyl oleate is the ester of retinol (q.v.) and oleic acid (q.v.).

Acetylated retino-amino acid compounds are prepared by reacting retinol with an N-acetylamino acid selected from the group of: N-Acety-L-alanine; N-Acetyl-L-arginine; N-Acetyl-L-aspartic acid; N-Acetyl-DL-asparagine; N-Acetyl-L-cysteine; N-Acetyl-L-selenocysteine; N-Acetyl-glycine; N-Acetyl-L-glutamic acid; N-Acetyl-L-glutamine; N-Acetyl-L-histidine; N-Acetyl-L-isoleucine; N-Acetyl-L-leucine; N-Acetyl-L-lysine; N-Acetyl-L-methionine; N-Acetyl-L-phenylalanine; N-Acetyl-L-proline; N-Acetyl-L-serine; N-Acetyl-L-threonine; N-Acetyl-L- tryptophan; N-Acetyl-L-tyrosine; N-Acetyl-L-valine; and N-Acetyl-β-alanine; N-Acetyl-phenylglycine; N-Acetyl-4-hydroxyphenylglycine; N-Acetyl-L-ornithine; and N-Acetyl-L-citrulline.

Non-limiting, but preferred acetylated, retino-amino acid compounds include: N-acetyl-O-retinyl glycine; N-acetyl-O-retinyl alanine; N-acetyl-O-retinyl isoleucine; N-acetyl-O-retinyl phenylalanine; N-acetyl-O-retinyl tryptopan; N-acetyl-O-retinyl glutamine; N-acetyl-O-retinyl histidine; N-acetyl-O-retinyl selenocysteine.

"Conjugated retinoic acid derivative" means monoglyceryl retinoate, diglyceryl retinoate, 1-oleoyl glyceryl retinoate, glyceryl diretinoate, arginine retinoate-1, O-diethyl-N-aspartyl retinoate, O-diethyl-N-glutamyl retinoate, ascorbyl retinoate, hydroxypinacolone retinoate, retinyl retinoate, and tocopheryl retinoate.

Preferred conjugated retinoic acid derivatives are monoglyceryl retinoate, diglyceryl retinoate, 1-oleyl glyceryl retinoate, and glyceryl diretinoate.

Monoglyceryl retinoate is the monoester formed by the reaction of glycerin (q.v.) with retinoic acid (q.v.).

Glyceryl diretinoate is the diester formed by the reaction of glycerin (q.v.) with retinoic acid (q.v.).

Ascorbyl retinoate is the product obtained by the reaction of retinoic acid (q.v.) and ascorbic acid (q.v.).

Retinyl retinoate is the ester of retinol (q.v.) and retinoic acid (q.v.).

Tocopheryl retinoate is the ester of tocopherol (q.v.) and retinoic acid (q.v.).

A first aspect of the present invention is directed to a lysophospholipid concentrate produced by a process comprising the steps of combining (i) a de-oiled lecithin and (ii) from about 0.5% to about 5% of an enzyme with PLA2 activity, resulting in a lysophospholipid concentrate has a hydrophilic-lipophilic balance (HLB) greater than about 12, preferably an HLB of about 14.

One preferred, but non-limiting example of an enzyme with PLA2 activity is MAXAPAL® A2 from DSM Food Specialties B.V. (Delft, Netherlands).

The lysophospholipid concentrate of the invention is further characterized by its constituents.

In certain preferred embodiments, the lysophospholipid concentrate (produced by reacting a de-oiled lecithin with an enzyme with PLA2 activity) contains (a) greater than about 20% lysophosphatidylcholine and (b) greater than about 2% LPA.

Importantly, the lysophospholipid concentrate used in the present invention is a pourable solution at or about room temperature.

Certain especially preferred embodiments of the present invention are directed to a lysophospholipid concentrate that contains LysoPC (as well as other phosphatides) having chains of linoleic acid or oleic acid at the C-1 position.

In certain embodiments of the invention, lysophosphatidic acid or an LPA-mimetic is added to the lysophospholipid concentrate.

In certain preferred embodiments, the lysophospholipid the LPA-mimetic is mono-oleoyl glyceryl phosphate.

In these preferred embodiments, a lysophospholipid concentrate is comprised of (i) from about 70% to about 100% of the reaction product of a de-oiled lecithin and from about 0.5 to about 2% of an enzyme with PLA2 activity and (ii) up to about 30% OGP.

The lysophospholipid concentrate of the invention is preferably used in dermatocosmetic compositions at a concentration of less than about 5%.

In daily-use, dermatocosmetic compositions (i.e., applied once daily), the lysophospholipid concentrate is preferably present at a concentration of less than about 1%, more preferably less than about 0.5%.

In once-weekly, dermatocosmetic compositions (i.e., applied one time over a period of seven consecutive days), the lysophospholipid concentrate is preferably present at a concentration of less than about 5%, preferably from about 2% to about 5%.

In dermatocosmetic compositions that are oil-in-water (O/W) emulsions, the lysophospholipid concentrate may be, and preferably is, the primary emulsifier.

In certain dermatocosmetic O/W emulsions, the lysophospholipid concentrate is the sole emulsifier.

The dermatocosmetic composition may contain one or more co-emulsifiers. Preferred, non-limiting co-emulsifiers, include cetyl phosphate, polyglyceryl-10-oleate, polyglyceryl-6-laurate, or oleoyl glyceryl citrate.

The lysophospholipid concentrate may be added to an already-formed emulsion, e.g., after the oil and water phases have been combined, often with heat and mixing. Preferably, the lysophospholipid concentrate is added during a "cool-down" phase.

In dermatocosmetic compositions that are anhydrous, the lysophospholipid concentrate may be added with or without co-emulsifiers.

The lysophospholipid concentrate of the invention is markedly different than lecithin in several respects. The HLB of lecithin is from about 4 to 8, depending on the source material, the extent to which the lecithin is de-oiled, and the relative concentrations of the phosphatides. In contrast, the lysophospholipid concentrate has an HLB of from about 12 to 14.

A further point of difference between lecithin and lysophospholipid concentrate of the present invention can be observed histologically.

When combined with a conjugated retinoid, the lysophospholipid concentrate of the present invention produces from about 50% to about 100% greater epidermal thickening than lecithin. Epidermal thickening of an anhydrous dermatocosmetic containing 1% retinyl linoleate and 0.2% lecithin (about 85% dioleoyl phosphatidyl choline) is less than an anhydrous dermatocosmetic containing 1% retinyl linoleate and 0.2% lysophospholipid concentrate (created by combining 98% lecithin having about 85% dioleoyl phosphatidyl choline with 2% PLA2).

Surprisingly and unexpectedly, when compared to DMSO delivered retinol at 5 ppm, a dermatocosmetic composition containing retinyl linoleate and a lysophospholipid concentrate of the present invention at a ratio of 1:0.4—a concentration expected to have one-half (50%) of the biological activity (dermal proliferation) of the DMSO delivered retinol at 5 ppm—had higher proliferative activity as measured in terms of levels of expression of five (5) proliferative/growth-factor related genes: HBGEF, TGF-beta 1, TGF alpha, FGF., and CSF2—as measured by DNA microarray assay.

| Gene | DMSO Delivered Retinol | Retinyl Linoleate + Lysophospholipid Concentrate |
| --- | --- | --- |
| HBEGF | −50% | +350% |
| TGF beta 1 | −50% | +50% |
| TGF alpha | +200% | +175% |
| FGF | −50% | +200% |
| CSF2 | −25% | +1100% |

It is reported in the scientific literature that TNF alpha orchestrates cutaneous responses to environmental damage and inflammation. See, e.g., T. Banno et al, *J. Biol. Chem. Vol.* 279, No. 31, pp. 32633-32642 (2004). Surprisingly, a dermatocosmetic composition of the present invention containing retinyl linoleate and a lysophospholipid concentrate of the present invention at a ratio of 1:0.4 produced 1/10 the amount of upregulation of TNF alpha gene as did a composition containing DMSO delivered retinol at 5 ppm in the cell culture media, further demonstrating that use of a lysophospholipid concentrate of the present invention in combination with a retinoid results in less dermal irritation than retinol.

Certain embodiments of the first aspect of the present invention are directed to use of the inventive lysophospholipid concentrate to increase the proliferative properties of a retinyl ester, in particular retinyl linoleate—a retinyl ester formed by the reaction of retinol and triglyceride oils of a plant rich in linoleic acid (as well as oleic acid).

In one set of embodiments, the inventive lysophospholipid concentrate surprisingly and unexpectedly increases the proliferative properties of retinyl safflowerate, a particularly preferred retinyl linoleate formed by the reaction retinol and safflower fatty acids.

It is known in the art that retinol requires conversion into retinoic acid (RA) to be receptor site active. Retinol is slower acting and thus less irritating that RA. It is also retinyl linoleate can increase epidermal thickening, but not to the extent of retinol. Retinyl linoleate is known to be less irritating than retinol. However, retinyl linoleate is also less proliferative than retinol.

The prior art teaches the use of dioleoyl phosphatidyl choline (DOPC), also known in the art as the primary component of de-oiled lecithin, to increase the proliferative properties of retinyl linoleate. Surprisingly and unexpectedly, when retinyl linoleate (1%) is combined with lysophospholipid concentrate of the present invention (0.2%) in an anhydrous carrier, a greater than 50% increase in epidermal thickening is observed versus retinyl linoleate (1%) and the same amount of DOPC (de-oiled lecithin) at 0.2%. Equally surprising and unexpected is that the addition of 0.2% lysophospholipid concentrate of the present invention to 1% retinyl linoleate resulted in a greater than 200% increase in epidermal thickening.

Moreover, when combined with 1% retinyl safflowerate in an anhydrous carrier, 0.2% lysophospholipid concentrate of the present invention produced complete differentiation with observably distinct BL, SL, GL, SC. In contrast, the retinyl linoleate at 1% and DOPC (de-oiled lecithin) at 0.2% in the same anhydrous carrier shows a poorly-defined supra-basal layer.

Certain especially preferred embodiments of the present invention are directed to a dermatocosmetic composition containing (i) the lysophospholipid concentrate of the invention and (ii) a retinyl lineolate, preferably retinyl safflowerate, wherein the lysophospholipid concentrate is present at a concentration of less than 2%, preferably less than 1%, still more preferably less than 0.5%, and the retinyl linoleate is present at a concentration of up to 5%.

In one especially preferred embodiment of this aspect of the invention, a dermatocosmetic composition contains the lysophospholipid concentrate and retinyl lineolate at a ratio of about 1:5.

Another embodiment of the first aspect of the present invention is directed to use of the inventive lysophospholipid concentrate to increase the proliferative properties of retinol in combination with at least one retinyl ester, preferably retinyl linoleate.

Preferably, a dermatocosmetic composition is comprised of the lysophospholipid concentrate (as described above) and both retinol and retinyl linoleate, preferably in a ratio of about 1:2.

Still more preferably, a dermatocosmetic composition contains: the lysophospholipid concentrate at a concentration of from about 0.1% to 5%, wherein the lysophospholipid concentrate is comprised of up to about 30% OGP; retinol at a concentration of from about 0.1% to about 1%; and a retinyl ester, preferably retinyl linoleate, at a concentration of from about 0.25% to about 5%, preferably from about 0.5% to 2.5%.

In daily-use dermatocosmetic compositions, retinol is preferably present at a concentration of from about 0.1% to 0.5%.

In once-weekly dermatocosmetic compositions, retinol is preferably present at a concentration of from about 0.5% to about 3.5%.

A second aspect of the present invention is directed to a low-urea retinoate produced by the reaction of (a) retinoic acid and (b) one or both of glycerine and/or a monoacyl-glyceride in the presence of a carbodiimide coupling agent. The resulting low-urea retinoate (xx) is a pourable solution at or about room temperature and (yy) has no significant visible precipitate.

By "low-urea retinoate" is meant a retinoate formed by the reaction of (a) retinoic acid and (b) one or both of glycerine and/or a monoacyl-glyceride in the presence of (c) a carbodiimide coupling agent.

A preferred carbodiimide coupling agent is dicyclohexylcarbodiimide (DCC).

Without the use of DCC, a side reaction occurs, producing significant amounts (>30%) of retinoyl urea—a compound that forms a precipitate and is not bioactive (i.e., does not act as a dermal proliferative).

Preferably, the low-urea retinoate is prepared in the presence of DCC and in the presence of p-toluene sulfonic acid (PTSA).

Surprisingly, and unexpectedly, addition of DCC and PTSA can reduce formation of retinoyl urea to levels of less than 2%, preferably less than 1%, more preferably less than 0.5%, and even more preferably less than 0.1%.

Alternatively, a low-urea retinoate—having levels of retinoyl urea of less than 2%, preferably less than 1%, more preferably less than 0.5%, and even more preferably less than 0.1%—can be formed by the reaction of (a) retinoic acid and (b) one or both of glycerine and/or a monoacyl-glyceride in the presence of (c) triphenylphosphone oxide and oxalyl chloride.

One particularly preferred low-urea retinoate is oleoyl glyceryl retinoate ("OGR"), produced by the reaction of (a) retinoic acid and (b) glyceryl oleate, preferably having a monoester content of greater than about 90%. OGR may be produced in the presence of (i) dicyclohexylcarbodiimide and p-toluene sulfonic acid or (ii) triphenylphosphone oxide and oxalyl chloride.

In emulsion embodiments of the present invention, co-emulsifiers are used at a concentration of not greater than about 3% by weight of the total emulsion. More preferably, co-emulsifiers are soluble in olive oil, macadameate, ethyl safflowerate.

Even more preferably, the co-emulsifier meets the criteria for the Natural Seal as promulgated by the Natural Products Association (Washington, D.C.).

Preferred co-emulsifiers are selected from the group consisting of sucrose esters, polyglyeryl oleates, polyglyeryl lactates, and oleyl steraryl citrates.

In preferred embodiments, the emulsion or anhydrous composition is comprised of an ethyl unsaturated fatty acid ester, an ester of ethyl alcohol and a plant-derived triglyceride oil with a high content (greater than 80%) of monoene (n-9) fatty acids or diene (n-6) fatty acid.

A preferred monoene (n-9) fatty acid is oleic acid —$CH_3(CH_2)_7CH=CH(CH_2)_7COOH$. Non-limiting examples of plant oils with high oleic acid content include peanut, olive and rapeseed oils.

A preferred diene (n-6) fatty acid is linoleic acid:

$CH_3(CH_2)_4CH=CHCH_2CH=CH(CH_2)_7COOH$.

Non-limiting examples plant oils with high linoleic acid content include soya, corn, sunflower and walnut oils.

Two particularly preferred ethyl unsaturated esters suitable for use in practicing the methods of the present invention are ethyl macadamiate and ethyl safflowerate—the esters of ethyl alcohol and the fatty acids derived, respectively, from macadamia seed oil and safflower seed oil.

In certain preferred embodiments, the methods of the present invention are practiced by concomitant administration of an unsaturated fatty acid ester of ascorbic acid (defined below) together with a retinoid, preferably a conjugated retinoid, and phosphatidic acid (or a derivative thereof).

By unsaturated fatty acid ester of ascorbic acid is meant the reaction product of an unsaturated fatty acid with the hydroxyl at the 6-position or, after blocking the 5,6 position, with the 2 or 3 position.

In one set of particularly preferred embodiments, an unsaturated fatty acid ester of ascorbic acid, a retinoid, preferably a conjugated retinoid, an anti-oxidant blend of rosemary extract, oleoyl quericitin, oleoyl pyrogallol and phosphatidic acid are administered topically in a single emulsion or anhydrous formulation, where the base of the emulsion or anhydrous formulation is comprised of at least one ethyl unsaturated ester, preferably ethyl macadamiate or ethyl safflowerate.

Non-limiting examples of preferred unsaturated fatty acid esters of ascorbic acid include ascorbyl linoleate, ascorbyl macadamiate, and ascorbyl safflowerate.

Ascorbyl linoleate ($C_{24}H_{38}O_7$) is an organic compound that conforms to the formula:

2 or 3 oleoyl ascorbate or Ascorbyl 2 or 3 oleate

Ascorbyl 6-Oleate

Ascorbyl macadamiate or ascorbyl safflowerate may be obtained by the reaction of (i) ascorbic acid and (ii) a fatty acid chloride of macadamia seed oil or safflower seed oil.

Alternatively, ascorbyl macadameate or ascorbyl safflowerate may be obtained by the condensation of (i) the fatty acid of macadamia seed oil or safflower seed oil and (ii) ascorbic acid in the presence of (iii) dicyclohexylcarbodiimide.

One skilled in the art of formulating skin care and dermatologic products understands that the exact composition of such formulations is subject to acceptable variation due to, for example, weighing and rounding errors, and that the weight percentages of ingredients in a particular batch or lot may not always add exactly to 100%. The percentages recited herein are therefore to be interpreted in light of this normal variation that would be expected by the skilled artisan.

EXAMPLES

The following examples are further illustrative of the present invention. The components and specific ingredients are presented as being typical, and various modifications can be derived in view of the foregoing disclosure within the scope of the invention.

| Concentrate Example #1 (C1) | |
|---|---|
| Lysolecithin (and) Lysophosphatidic Acid (LPA) (and) Oleoyl Glyceryl Phosphate (OGP) (5:1:1) | 10.00 |
| Ascorbyl Safflowerate | 1.00 |
| Tocopheryl Safflowerate | 0.25 |
| Rosemary Extract | 0.25 |
| 80 parts Ethyl Macadameate to 20 parts Safflower Oil (enzymatically-treated to produce MAGs and DAGs) | 38.50 |
| Retinyl Safflowerate/rosemary extract/oleoyl quercitin/oleoyl pyrogallol 49/0.3/0.3/0.3 | 50 |

| Concentrate Example #2 - used in thickened anhydrous gel (triglyceride or ethyl ester) | |
|---|---|
| C1 | 3.0 |
| Ethyl Safflowerate | QS |
| Dextran myristate | 2.0-10.0 |

| Concentrate Example #3 - use in anhydrous silicone gel | |
| --- | --- |
| C1 | 3.00 |
| 80 parts Ethyl Macadameate to 20 parts Safflower Oil (enzymatically-treated to produce MAGs and DAGs) | 15.00-20.00 |
| Silicone polymer gel (Dow 8541) | QS |

| Formulation Example #1 | |
| --- | --- |
| Water | 90.0 |
| Ethyl Safflowerate | 7.9 |
| Ascorbyl Linoleate | 0.4 |
| Tocopheryl Linoleate | 0.2 |
| Retinyl Linoleate | 1.0 |
| Oleyl Glyceryl Phosphate | 0.5 |
| SEQ ID 1 | 30 ppm |

| Formulation Example #2 | |
| --- | --- |
| Water | 86.0 |
| Ethyl Safflowerate | 7.9 |
| Ascorbyl Linoleate | 0.4 |
| Tocopheryl Linoleate | 0.2 |
| Retinyl Linoleate | 1.0 |
| Oleyl Glyceryl Phosphate | 0.5 |
| SEQ ID 3 | 30 ppm |
| Polyglyceryl 3 Polyriccinoleate | 2 |
| Polyglyceryl 5 Oleate | 2 |

| Formulation Example #3 | |
| --- | --- |
| Vitamin E Acetate | 0.19 |
| Vitamin A Palmitate | 0.38 |
| Vitamin K1 | 0.04 |
| Vitamin D3 | 0.04 |
| Panthenol | 0.08 |
| Niacinamide | 0.04 |
| Ethyl Macadameate | 7.50 |
| Polyglyceryl-3 Polyricinoleate | 1.50 |
| Polyglyceryl-5 Oleate | 1.50 |
| Retinyl Oleate | 1.00 |
| Ethyl Safflowerate | 2.50 |
| Oleyl Glyceryl Phosphate (LPA) | 0.50 |
| Water | 84.73 |

In-Vivo Testing Example #1

Five mice are used in the following studies. The back of each mouse is shaved and divided into two test sites—A and B. Tissue from each of these sites is excised and fixed in formalin for 24 hours. Tissue samples are embedded in paraffin wax, cut into five sections, and plated on a slide. The plated sections are then stained in hematoxylin and eosin. Image acquisition of H&E stained tissue sections is performed using a Leica microscope at 60× (Leica Microsystems, Bannockburn, Ill.) with a CCD camera. Images are analyzed with computer software; the thickness of the epidermis is determined by hand-drawn line segments connecting the intact stratum corneum to the dermal-epidermal junction. Software records the length of each line segment drawn. Twenty line segments were drawn on each of the five sections per slide (for a total of 100 measurements).

In-Vivo Testing Example #2

Adults between the ages of 35 and 55 (inclusive) meeting the following criteria are recruited to participate in a clinical study: general good health (no physical required); noticeable fine line and wrinkles on the face and/or sagging facial skin (for qualification purposes only); willingness to sign Informed Consent and anticipated ability to follow, participate in, and complete the study by following all study directions, returning for all visits, and applying test/control products per instructions. Individuals meeting one or more of the following conditions are excluded from study enrollment: diagnosed with acne, active atopic dermatitis/eczema or psoriasis, or other skin disease; known sensitivity to cosmetics or personal care products; visible sunburn, suntan or planning a vacation with sun-exposure or planning the use of a tanning booth during the course of the study; currently under treatment for asthma or diabetes; past treatment or history of any type of cancer; pregnant or planning to become pregnant during the course of the study; using medications that might confound the test results including steroidal/non-steroidal anti-inflammatory drugs or antihistamines; laser resurfacing or dermabrasion procedure on the face in the past 2 years; chemical face peel (deep peel in the past 1 year; superficial peel in the past two months); surgical "cosmetic" procedure on the face within the past 10 years.

Enrolled subjects are visually graded at based and at defined time intervals for skin redness/irritation and skin dryness by an expert grader for using a four-point Visual Analogue Scale (VAS). Redness/Irritation is graded on the following VAS: 0=no to very little erythema, slight scaling; 1=weak erythema, possibly slight infiltration; 2=marked erythema, infiltration, possibly vesicles and crusting; 3=pronounced erythema, infiltration, possibly vesicles, bullae, pustules and/or pronounced crusting. Skin dryness is graded from 0=no evidence of dryness to 4=severe flaking, peeling and/or fissures.

To supplement VAS redness/irritation assessment, clinical photographs are taken at study points and evaluated using image analysis software, for example VISIA® from Canfield Scientific.

Additionally, skin irritation is assessed based on biomarkers (cytokines and total protein) according to the following test method: the adhesive side of Sebutape® (Cu-Derm, Dallas, Tex.) is applied to treated and untreated areas of skin for a one minute, using gloved hands to avoid cross contamination of skin proteins. Tape is removed from the skin using blunt forceps and placed flat into individually labeled glass vials, placed on dry ice, and then transferred to a freezer for storage until biomarker analysis.

Tapes are thawed to room temperature and immersed for one hour, non-adhesive side facing outward, in 1 ml of 1× Dulbecco's phosphate buffered saline prepared in deionized sterile water (pH 7.0±0.2). The tapes are then sonicated for 10 minutes in a room-temperature water bath, vortexed vigorously, and re-frozen overnight.

Tape are again thawed, vortexed and then centrifuged for one minute to recover tissue extracted onto the tape. Extracts are analyzed for human IL-1a, IL-1RA, and IL-8 using enzyme-linked immunosorbent assay (ELISA) kits. Cytokine levels are expressed as interleukin levels (in picograms) per microgram of total protein recovered from each Sebutape. Total protein is measured using Pierce enhanced microtiter assay (Pierce, Rockford, Ill., USA) with bovine serum albumin as the standard.

Reduction in the rate of transepidermal water loss and improvement in skin moisture content are measured, respectively, with an evaporimeter and corneometer. The operating principles of these instruments and methods of use have previously been described and are well known to the person having ordinary skill in the art.

Test subjects are randomly divided into two groups, and instructed to apply the product as provided (test or control) twice a day for two weeks to the lower lateral area of one leg. Panelists refrain from extended sun exposure and usage of any moisturizers, shaving cream, anti-itch or other skincare products on their legs one week prior to baseline visit until the end of study. Subjects wash their lower legs using Ivory® soap bar approximately 1 hour prior to each study visit and abstain from shaving lower legs within forty-eight hours prior to all visits.

Skin thickness is measured by a 20 MHz high-resolution ultrasound scanner (Dermascan®, Cortex Technology, Hadsund, Denmark) capable of visualizing layers and structures to a depth of 50 mm.

Degree of skin flaking/peeling can be measured according to the following clinical test method: After completing an equilibration period of fifteen minutes, 2 mg of a test product or control seeded with dansyl chloride is applied to both volar forearms and allowed to dry for 15 minutes. Immediately thereafter, fifteen individual tape strips are applied and the amount of dansyl chloride removed on each tape strip is graded under a Wood's Lamp.

Skin flaking/peeling can also be measured by the following method: A suitable corneocyte staining dye (e.g., gentian violet) is applied to a 2 to 5 cm diameter spot on the skin (e.g., arm or leg) and left on for 5 minutes to ensure uniform staining of the skin surface cells. Excess dye is then washed away by rinsing the spot under running water at 35° C. for 30 seconds without rubbing the skin. Test products (used in practicing methods of the invention) are applied to the stained sites. D-Squame tape, CuDerm® available from CuDerm Corp. (Dallas, Tex.), is applied using uniform pressure for 30 seconds, and then removed. The D-Squame tape is imaged using a digital camera. The image is analyzed using image analysis software for area covered/total intensity of stained cells. A non-limiting example of suitable image analysis software is available under the tradename Optimas® from Media Cybernetics (Silver Spring, Md.).

The invention claimed is:

1. A lysophospholipid concentrate comprised of
   (a) a de-oiled lecithin source reacted with 0.5% to 2% of an enzyme with phospholipase A2 (PLA2) activity resulting in a lysophosphatide having at least greater than 20% lysophosphatidyl-choline; and
   (b) a retinyl ester selected from retinyl linoleate, glyceryl diretinoate, glyceryl oleoyl retinoate, diretinyl succinate, acetyl-n-phenylalanine retinoate, retinyl phosphate, glyceryl mono retinoate, arginine retinoate-1, O-diethyl-N-aspartyl retinoate, O-diethyl-N-glutamyl retinoate, ascorbyl retinoate, hydroxypinacolone retinoate, retinyl retinoate, and tocopheryl retinoate;
   wherein the lysophospholipid concentrate is a pourable, homogenous mixture/solution at or about room temperature.

2. The lysophospholipid concentrate of claim 1 has greater than 10% of lysophatitidic acid, monooleoyl glyceryl phosphate, or its cyclic derivatives of monooleoyl glyceryl phosphate.

3. The lysophospholipid concentrate of claim 1 further comprising an unsaturated fatty acid ester of ascorbic acid selected from the group consisting of ascorbyl linoleate, ascorbyl macadameate, ascorbyl safflowerate, ascorbyl 2 oleate, ascorbyl 3 oleate, and ascorbyl 6 oleate.

4. The lysophospholipid concentrate of claim 2 further comprising an unsaturated fatty acid ester of ascorbic acid selected from the group consisting of ascorbyl linoleate, ascorbyl macadameate, ascorbyl safflowerate, ascorbyl 2 oleate, ascorbyl 3 oleate, and ascorbyl 6 oleate.

5. The lysophospholipid concentrate of claim 1 further comprising a co-emulsifier selected from the group of cetyl phosphate, polyglyceryl-10-oleate, polyglyceryl-6-laurate, or oleoyl glyceryl citrate.

6. The lysophospholipid concentrate of claim 1 further comprising an ethyl unsaturated fatty acid formed by reacting ethanol with a plant-derived triglyceride oil having a content of greater than 80% of (a) monoene fatty acids or (b) diene fatty acids.

7. The lysophospholipid concentrate of claim 6 wherein the source of the plant-derived triglyceride oil is soya, corn, sunflower, walnut, peanut, olive, rapeseed, macadamia, or safflower.

8. A dermatocosmetic composition comprised of the lysophospholipid concentrate of claim 1.

9. The dermatocosmetic composition of claim 8 wherein the lysophospholipid concentrate has greater than 10% of lysophatitidic acid, mono-oleoyl glyceryl phosphate, or cyclic derivatives of monooleoyl glyceryl phosphate.

10. The dermatocosmetic composition of claim 8 further comprising an unsaturated fatty acid ester of ascorbic acid selected from the group consisting of ascorbyl linoleate, ascorbyl macadameate, ascorbyl safflowerate, ascorbyl 2 oleate, ascorbyl 3 oleate, and ascorbyl 6 oleate.

11. The dermatocosmetic composition of claim 8 further comprising an ethyl unsaturated fatty acid formed by reacting ethanol with a plant-derived triglyceride oil having a content of greater than 80% of (a) monoene fatty acids or (b) diene fatty acids.

12. The dermatocosmetic composition of claim 11 wherein the source of the plant-derived triglyceride oil is soya, corn, sunflower, walnut, peanut, olive, rapeseed, macadamia, or safflower.

13. The dermatocosmetic composition of claim 8 further comprising a co-emulsifier selected from the group of cetyl phosphate, polyglyceryl-10-oleate, polyglyceryl-6-laurate, or oleoyl glyceryl citrate.

* * * * *